US008747876B2

(12) United States Patent
Park

(10) Patent No.: US 8,747,876 B2
(45) Date of Patent: Jun. 10, 2014

(54) OLEOPHILIC ANTIMICROBIAL COMPOSITION

(75) Inventor: Chung Kwon Park, Busan (KR)

(73) Assignee: Thermolon Korea Co., Ltd., Jungang-dong, Jung-gu, Busan (KR)

( * ) Notice: Subject to any disclaimer, the term of this patent is extended or adjusted under 35 U.S.C. 154(b) by 0 days.

(21) Appl. No.: 12/990,028

(22) PCT Filed: Aug. 27, 2010

(86) PCT No.: PCT/KR2010/005787
§ 371 (c)(1),
(2), (4) Date: Dec. 14, 2012

(87) PCT Pub. No.: WO2011/152591
PCT Pub. Date: Dec. 8, 2011

(65) Prior Publication Data
US 2013/0084321 A1    Apr. 4, 2013

(30) Foreign Application Priority Data
Jun. 3, 2010 (KR) .......................... 10-2010-0052480

(51) Int. Cl.
*A01N 25/08* (2006.01)
*A01N 59/16* (2006.01)
(52) U.S. Cl.
USPC .......................................... 424/409; 424/618
(58) Field of Classification Search
None
See application file for complete search history.

(56) References Cited

U.S. PATENT DOCUMENTS

2009/0117087 A1 * 5/2009 Carroll et al. ................ 424/93.7

FOREIGN PATENT DOCUMENTS

| KR | 100695492 B1 * | 3/2007 | |
| WO | WO 2010079882 A1 * | 7/2010 | ................ B82B 3/00 |

OTHER PUBLICATIONS

English Machine Language Translation of KR 10-0695492 B1.*
English Machine Language Translation of WO 2010/079882 A1.*

* cited by examiner

*Primary Examiner* — Michael G Hartley
*Assistant Examiner* — Sun Y Kim
(74) *Attorney, Agent, or Firm* — John K. Park; Park Law Firm

(57) ABSTRACT

The present invention relates to an oleophilic antimicrobial composition comprising silica nanotubes containing silver nanoparticles. The composition is added to an oil-based composition, such as an oil-based paint, a ceramic composition or a fiber coating compositions, immediately before the use of the oil-based composition, such that the contact time of the silver nanoparticles with the organic solvent contained in the oil-based composition is shortened to inhibit the oxidation of the silver nanoparticles. In addition, the composition has improved antimicrobial effects due to the excellent dispersibility of the silver nanoparticles, because the silver nanoparticles do not agglomerate in any solvent due to the silica nanotube structures, unlike spherical silica structures.

1 Claim, 2 Drawing Sheets

OLEOPHILIC ANTIMICROBIAL COMPOSITION

TECHNICAL FIELD

The present invention relates to an oleophilic antimicrobial composition comprising silica nanotubes containing silver nanoparticles. The oleophilic antimicrobial composition according to the present invention is added to an oil-based composition, such as an oil-based paint composition, a ceramic composition or a fiber coating composition, immediately before the use of the oil-based composition, such that the contact time of the silver nanoparticles with the organic solvent contained in the oil-based composition is shortened to inhibit the oxidation of the silver nanoparticles. Also, the antimicrobial composition according to the present invention has improved antimicrobial effects due to the excellent dispersibility of the silica nanotubes.

BACKGROUND ART

Recently, as interest in environment and human health has gradually increased, there has been increased consumption of antimicrobial-treated products, including baby and children's products and utensils, such as chopping boards, food storage containers or scrubbers, which were treated with antimicrobial agents to inhibit the multiplication of bacteria or fungi. This antimicrobial treatment has been applied to a wide range of products, including daily-use articles, household appliances or building materials.

As the demand for such products treated with antimicrobial agents has increased, a variety of highly functional antimicrobial compositions have been developed. With respect to patent documents that disclose such antimicrobial compositions, Korean Patent Registration No. 0606253 discloses a disinfectant/antimicrobial and deodorant aqueous composition for fabric deodorizers, which comprises, as active ingredients, nano silver ions supported on an inorganic material such as calcium oxide, silica, alumina or zeolite, a persimmon extract, perfume, a surfactant and ethanol. This composition has disinfectant/antimicrobial functions together with deodorizing functions and is intended for use in fabric deodorizers.

Korean Patent Laid-Open Publication No. 2007-0119219 discloses a coating composition for antimicrobial and deodorizing applications, which contains, based on 100 parts by weight of an inorganic binder, 5-40 parts by weight of a functional spherical silica having silver nanoparticles supported thereon, the spherical silica having a mean particle diameter of 2-5 μm. This composition is an antimicrobial composition intended for use in printers or copiers and has limited applications.

Particularly in the case of, for example, paints, antimicrobial paints comprising an antimicrobial agent containing silver nanoparticles are coming into the market. However, in the case of such antimicrobial paints, the silver nanoparticles are oxidized by the solvent contained in the paint composition, thus making it difficult to effectively exhibit the antimicrobial activity of the antimicrobial agent. If the antimicrobial agent is added in large amounts in order to overcome this problem associated with the oxidation of silver nanoparticles, the silver nanoparticles will be likely to agglomerate, and the coating film formed of the paint composition can be discolored due to the increase in the content of the metal component. In addition, the coating film will be thicker, and thus be easily peeled off.

For these reasons, there have been developed and used antimicrobial agents comprising silica carriers which contain silver nanoparticles in their fine pores as disclosed in the above-mentioned patents in order to increase the dispersibility of the silver nanoparticles. However, because the silica carriers are spherical in shape, the agglomeration of the silver nanoparticles still occurs, and the dispersibility of the silver nanoparticles is low such that the microbial agents have insufficient antimicrobial activity.

DISCLOSURE OF INVENTION

The present invention has been made in order to solve the above-described problems occurring in the prior art, and it is an object of the present invention to provide an oleophilic antimicrobial composition which comprises silica nanotubes containing silver nanoparticles and which is added to an oil-based composition, such as an oil-based paint composition, a ceramic composition or a fiber coating compositions, immediately before the use of the oil-based composition, such that the contact time of the silver nanoparticles with the organic solvent contained in the oil-based composition is shortened to inhibit the oxidation of the silver nanoparticles so as to improve the antimicrobial effect of the microbial composition.

Another object of the present invention is to provide an oleophilic antimicrobial composition comprising silver nanoparticle-containing silica nanotubes dispersed in an organic solvent, wherein when the oleophilic antimicrobial composition is added to an oil-based composition such as an oil-based paint composition or a printing ink composition, the silver nanoparticles show excellent dispersibility, because the silver nanoparticles do not agglomerate in the organic solvent of the oil-based composition due to the silica nanotube structures, unlike spherical silica structures.

To achieve the above objects, the present invention provides an oleophilic antimicrobial composition wherein silica nanotubes containing silver nanoparticles are dispersed in an organic solvent.

In the present invention, the silica nanotubes preferably have fine pores formed therein and having a size of 30-50 nm, and each of the silica nanotubes preferably has a total length of 1-30 μm. Also, the content of the silver nanoparticles in the silica nanotubes is preferably 20000~100000 ppm.

In the present invention, the organic solvent is preferably propylene glycol methyl ether acetate.

Also, the silica nanotubes are preferably contained in an amount of 35-45 parts by weight based on 100 parts by weight of the organic solvent, and the oleophilic antimicrobial composition preferably further contains a wetting/dispersing agent in an amount of 20-30 parts by weight based on 100 parts by weight of the organic solvent.

EFFECT OF THE INVENTION

The oleophilic antimicrobial composition according to the present invention is added to an oil-based composition, such as an oil-based paint composition, a ceramic composition or a fiber coating composition, immediately before the use of the oil-based composition, such that the contact time of the silver nanoparticles of the oleophilic antimicrobial composition with the organic solvent contained in the oil-based composition is shortened to inhibit the oxidation of the silver nanoparticles. Also, the oleophilic antimicrobial composition according to the present invention has improved antimicrobial activity due to the excellent dispersibility of the silver nanoparticles, because the silver nanoparticles do not agglomerate in any solvent due to the nanotube structures, unlike spherical silica structures.

BEST MODE FOR CARRYING OUT THE INVENTION

Figure 1:
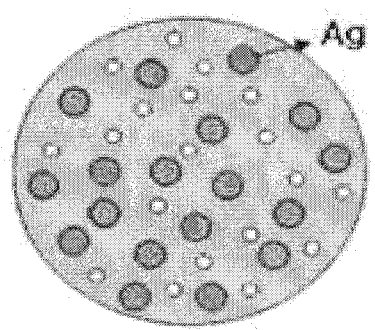
FIG. 1 is a cross-sectional view showing a porous silica having silver nanoparticles supported thereon according to the prior art.

Now, a preferred embodiment for carrying out the present invention to achieve the above effect of the invention will be described hereinafter in more detail with reference to FIGS. 1 to 4. In the following detailed description, explanation on the construction and operation which those skilled in the art can easily understand will be briefly made or will be omitted to avoid redundancy.

The oleophilic antimicrobial composition according to the present invention comprises silica nanotubes containing silver nanoparticles and is added to oil-based compositions, such as oil-based paints, fiber coating compositions or synthetic resin compositions, immediately before the use of the oil-based compositions, such that the contact time of the silver nanoparticles with the organic solvent contained in the oil-based compositions is shortened to inhibit the oxidation of the silica nanoparticles. Also, the oleophilic antimicrobial composition according to the present invention has improved antimicrobial activity due to the excellent dispersibility of the silica nanotubes.

Also, as the silica nanotubes containing silica nanoparticles in the present invention, silver nanoparticle-containing silica nanotubes having high dispersibility (hereinafter referred to as "silica nanotubes"), disclosed in Korean Patent Application No. 10-2009-0000961 previously filed in the name of the applicant, are preferably used.

The silica nanotubes contains silver nanoparticles having fine pores formed therein and having a size of 30-50 nm, and each of the silica nanotubes has a total length of about 1-30 μm. When the silica nanotubes are added to oil-based compositions, such as oil-based paints, printing inks or synthetic resin compositions, they have excellent dispersibility, unlike spherical silica, because the silica nanoparticles do not agglomerate in the solvent of the oil-based compositions due to the silica nanotube structures.

In the present invention, the content of the silver nanoparticles in the silica nanotubes is preferably 20000-100000 ppm. If the content of the silver nanoparticles is less than 20000 ppm, the antimicrobial effect thereof will be insufficient, and if the content of the silver nanoparticles is more than 100000 ppm, the antimicrobial activity thereof will not markedly increase while the production cost of the silica nanotubes will increase, resulting in disadvantages in economic terms.

Also, the silica nanotubes according to the present invention are preferably contained in an amount of 45-55 parts by weight based on 100 parts by weight of the organic solvent. The content of the silica nanotubes is lower than the lower limit of the above-specified range, the antimicrobial activity of the composition will be decreased, and if the content of the silica nanotubes is higher than the higher limit of the above-specified range, it will cause inconvenience due to caking caused by the agglomeration of the microbial composition.

Moreover, the organic solvent that is used in the present invention is involved in the adjustment of viscosity and the workability of the oleophilic antimicrobial composition and is suitable for use in oily compositions such as oily paints or oily inks.

The organic solvent that is used in the present invention is preferably at least one selected from the group consisting of propylene glycol methyl ether acetate (hereinafter, referred to as 'PMA'), butyl cabitol, butyl acetate and ethyl acetate. More preferably, Dowanol PMA (DOW) is used.

Particularly, the Dowanol PMA (DOW) is widely used in organic solvent systems due to its excellent solubility and shows excellent solubility for a wide range of resins, such as acrylic, epoxy, alkyd and polyester resins. Thus, it increases compatibility with the additives of resin-free type added.

Accordingly, the oleophilic antimicrobial composition according to the present invention shows excellent compatibility with oil-based compositions due to the organic solvent PMA.

Moreover, the oleophilic antimicrobial composition preferably additionally contains a wetting/dispersing agent in order to increase the dispersibility of the composition when it is added to oil-based compositions such as oil-based paints, oil-based inks or synthetic resin compositions.

The wetting/dispersing agent is an additive having both a wetting function and a dispersing function and serves to increase the dispersibility of the silica nanotubes in oil-based compositions and to inhibit the agglomeration of the silica nanotubes. Namely, the wetting/dispersing agent has a surfactant structure, i.e., both a polar hydrophilic group and a non-polar hydrophobic structure in one molecule, and increases the interfacial tension between the surface of the silica nanotubes and the resin solution to increase the dispersibility of the silica nanotubes. Thus, it accelerates the wetting of the silica nanotubes to improve the dispersibility of the oleophilic antimicrobial composition in the oil-based composition.

The content of the wetting/dispersing agent in the oleophilic antimicrobial composition is preferably 20-30 parts by weight based on 100 parts by weight of the organic solvent. If the content of the wetting/dispersing agent is less than 20 parts by weight, the dispersibility of the silica nanotubes in the oil-based composition will be reduced, and if the content of the wetting/dispersing agent is more than 30 parts by weight, it will not markedly improve the dispersibility of the silica nanotubes in the oil-based composition but rather change the physical properties of the oil-based composition and cause disadvantages in terms of cost.

The wetting/dispersing agent that is used in the present invention is preferably at least one selected from the group consisting of alkylammonium salt copolymer compounds, polyester/polyether-based compounds, copolymers containing a phosphoric acid group, and copolymers having a polar/non-polar amine group. Preferred examples of the wetting/dispersing agent that is used in the present invention include DISPERBYK-180, 2050, 2025, and 163 (BYK Chemie GmbH, Germany).

The oleophilic antimicrobial composition according to the present invention, which has the above-described components, is added to oil-based compositions, such as oil-based paints, oil-based inks or ceramic compositions, immediately before the use of the oil-based compositions.

Hereinafter, the present invention will be described in further detail with reference to Examples. However, the scope of the present invention is not limited only to these examples.

1. Preparation of Oleophilic Antimicrobial Compositions

Example 1

45 parts by weight of silica nanotubes containing silver nanoparticles, and 20 parts by weight of the wetting/dispersing agent DISPERBYK-180 (BYK Chemie GmbH, Germany) were mixed and dispersed in 100 parts by weight of the organic solvent Dowanol PMA (DOW) to prepare an oleophilic antimicrobial composition.

The silica nanotubes used had fine pores formed therein and having a size of 30-50 nm. Each of the silica nanotubes had a total length of 1-30 μm. The average content of the silver nanoparticles in the silica nanotubes was 30000 ppm.

Figure 2:
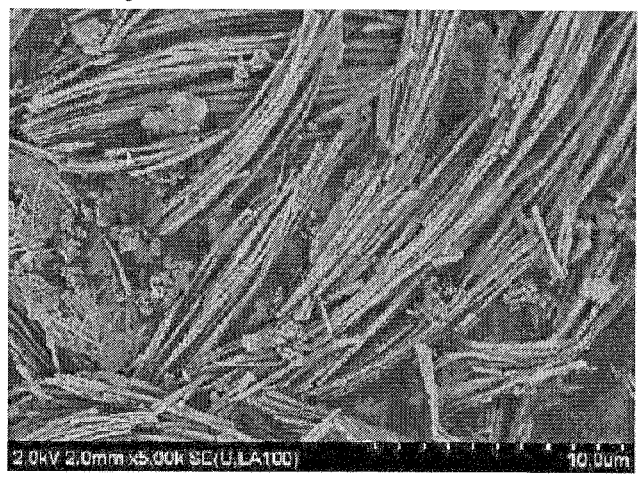
FIG. 2 is a TEM photograph of silver nanoparticles-silica nanotubes according to the present invention.
Figure 3:
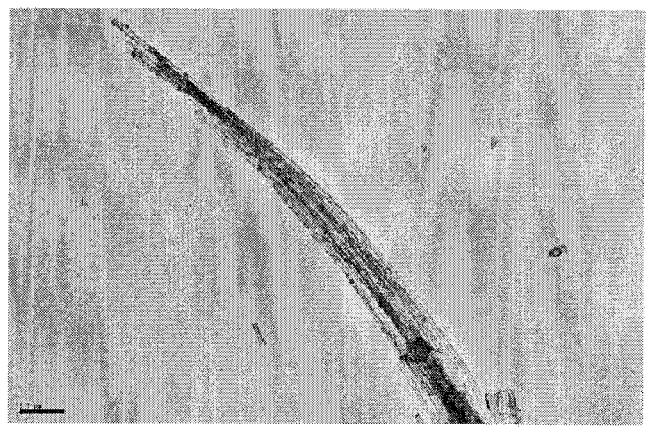
FIG. 3 is an SEM photograph of silver nanoparticles-silica nanotubes according to the present invention.
Figure 4:
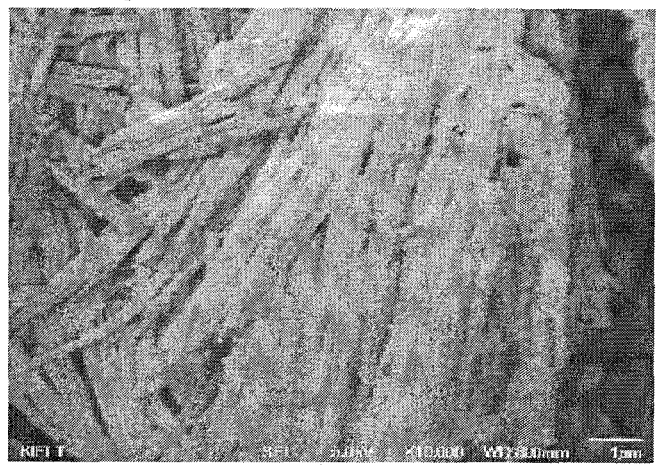
FIG. 4 is an SEM-EDX photograph taken after centrifugation of silver nanoparticles-silica nanotubes according to the present invention.

The silica nanotubes used in Example 1 of the present invention had the crystal structure shown in FIGS. 2 and 3. As can be seen in the photograph of FIG. 4 and from the results of analysis, the silver nanoparticles were not separated from the silica nanotubes.

Comparative Example 1

An oleophilic antimicrobial composition was prepared in the same manner as Example, except that silver nanoparticle-containing spherical silica particles having a mean particle size of 2-5 μm were used instead of the silver nanoparticle-containing silica nanotubes.

2. Preparation of Paint Compositions Having Antimicrobial Properties, and Samples 1 part by weight f each of the oleophilic antimicrobial compositions prepared in Example 1 and Comparative Example 1 was added to 100 parts by weight of acrylic urethane, thus preparing acrylic urethane paint compositions. Each of the prepared paint compositions was applied to a synthetic resin film to a thickness of 60 μm (dry basis).

3. Evaluation of Antimicrobial Properties

Antimicrobial tests against *Escherichia coli* and *Staphylococcus aureus* were carried out in accordance with JIS Z 2801: 2006 (antimicrobial processed products, antimicrobial test method, antimicrobial effect), and the test results are shown in Table 1 below.

The microbial strains used were *Escherichia coli* ATCC 8739 and *Staphylococcus aureus* ATCC 6538p.

Also, the antimicrobial activity (R) of each sample was calculated according to the following equation:

$$\text{Antimicrobial activity}(R) = [\log(B/A)/\log(C/A)] = [\log(B/C)]$$

where A: average number of viable cells on unprocessed sample immediately after inoculation with bacteria, B: average number of viable cells on unprocessed sample 24 hours after inoculation with bacteria, and C: average number of viable cells on antimicrobial-processed sample 24 hours after inoculation with bacteria.

TABLE 1

| Test Items | Classification of Samples | Example 1 | Comparative Example 1 |
|---|---|---|---|
| Antimicrobial Test (*E. coli*) | A | $1.5 \times 10^5$ CFU/sample | $1.5 \times 10^5$ CFU/sample |
| | B | $1.2 \times 10^6$ CFU/sample | $1.4 \times 10^6$ CFU/sample |
| | C | <10(less than 10) CFU/sample | $1.3 \times 10^4$ CFU/sample |
| | Antimicrobial activity(R) | 5 log | 2 log |
| Antimicrobial Test (*S. aureus*) | A | $1.6 \times 10^5$ CFU/sample | $1.4 \times 10^5$ CFU/sample |
| | B | $1.7 \times 10^5$ CFU/sample | $2.1 \times 10^5$ CFU/sample |
| | C | <10(less than 10) CFU/sample | $2.6 \times 10^3$ CFU/sample |
| | Antimicrobial activity(R) | 4 log | 2 log |

As can be seen in Table 1 above, the antimicrobial activity (R) of Example 1 against *E. coli* was log 5, indicating an antimicrobial effect of more than 99.999%, and the antimicrobial activity (R) of Example 1 against *S. aureus* was log 4, indicating an antimicrobial effect of more than 99.99%, whereas the antimicrobial activity (R) of Comparative Example 1 against *E. coli* was log 2, indicating an antimicrobial effect of 99%, and the antimicrobial activity (R) of Comparative Example 1 against *S. aureus* was log 2, indicating an antimicrobial effect of 99%.

Accordingly, as shown in Table 1 above, I was found that the oleophilic antimicrobial composition according to the present invention comprising the silica nanotubes had excellent antimicrobial activities against both *E. coli*. and *S. aureus* compared to the microbial composition of Comparative Example 1 comprising the spherical silica particles. The reason why Example 1 and Comparative Example 1 showed the different results despite the same test conditions is believed to be that the silica nanotubes had excellent dispersibility in the oil-based composition compared to the spherical silica particles of Comparative Example 1.

MODE FOR INVENTION

The present invention provides an oleophilic antimicrobial composition wherein silica nanotubes containing silver nanoparticles are dispersed in an organic solvent. In the present invention, the silica nanotubes have fine pores formed therein and having a size of 30-50 nm, and each of the silica nanotubes has a total length of 1-30 μm. Also, the content of the silver nanoparticles in the silica nanotubes is 20000~100000 ppm.

INDUSTRIAL APPLICABILITY

The oleophilic antimicrobial composition according to the present invention is added to an oil-based composition, such as an oil-based paint composition, a ceramic composition or a fiber coating composition, immediately before the use of the oil-based composition, such that the oleophilic antimicrobial composition has improved antimicrobial activity due to the excellent dispersibility of the silver nanoparticles, because the silver nanoparticles do not agglomerate in any solvent due to the nanotube structures, unlike spherical silica structures.

Although the preferred embodiments of the present invention have been described for illustrative purposes, those skilled in the art will appreciate that various modifications, additions and substitutions are possible, without departing from the scope and spirit of the invention as disclosed in the accompanying claims.

The invention claimed is:

1. An oleophilic antimicrobial composition comprising:

silica nanotubes containing silver nanoparticles dispersed in an organic solvent; and a wetting and dispersing agent, wherein the silica nanotubes have fine pores formed therein, each of the fine pores having a size of 30-50 nm and each of the silica nanotubes having a total length of 1-30 µm, wherein the content of the silver nanoparticles in the silica nanotubes is 20000-100000 ppm, wherein the silica nanotubes are contained in an amount of 45-55 parts by weight based on 100 parts by weight of the organic solvent, wherein the organic solvent is at least one selected from the group consisting of propylene glycol methyl ether acetate (hereinafter, referred to as 'PMA'), butyl cabitol, butyl acetate and ethyl acetate, wherein the wetting and dispersing agent is provided in an amount of 20-30 parts by weight based on 100 parts by weight of the organic solvent, and wherein the wetting and dispersing agent is at least one selected from the group consisting of alkylammonium salt copolymer compounds, polyester and polyether-based compounds, copolymers containing a phosphoric acid group, and copolymers having a polar or non-polar amine group.

* * * * *